United States Patent [19]

Bear et al.

[11] Patent Number: 4,670,396
[45] Date of Patent: Jun. 2, 1987

[54] VERTICAL CULTURE SYSTEM WITH REMOVABLE CULTURE UNIT

[75] Inventors: Mark P. Bear, Newburyport; F. Howard Schneider, Cambridge, both of Mass.

[73] Assignee: Bioassy Systems Corporation, Woburn, Mass.

[21] Appl. No.: 729,685

[22] Filed: May 2, 1985

[51] Int. Cl.[4] .............................................. C12M 3/00
[52] U.S. Cl. .................................... 435/285; 435/287; 435/310
[58] Field of Search ............... 435/292, 293, 294, 299, 435/310, 285, 300, 301, 287; 206/569, 804, 438; 220/355

[56] References Cited

U.S. PATENT DOCUMENTS

3,849,256 11/1974 Linder ................................. 435/300
4,125,436 11/1978 Liner .................................... 435/287

*Primary Examiner*—Samuel Scott
*Assistant Examiner*—Noah Kamen
*Attorney, Agent, or Firm*—Joseph S. Iandiorio; Douglas E. Denninger

[57] ABSTRACT

A vertical culture system including a culture tube having an opening and a bottom opposite the opening and a removable culture unit which has a platform and an elongate handle for disposing the platform proximate the tube bottom and for permitting removal of the culture unit. The culture system also includes a culture substrate carried by the platform and closure means for sealing the tube. The culture system may further include a volume retention element disposed within the culture tube.

25 Claims, 7 Drawing Figures

VERTICAL CULTURE SYSTEM WITH REMOVABLE CULTURE UNIT

FIELD OF INVENTION

This invention relates to a cell culture apparatus, and more particularly to a vertical culture system having a culture tube and a culture unit which carries a culture substrate and permits facile removal of the substrate from the tube.

BACKGROUND OF INVENTION

Cultures containing mammalian cells provide useful information in diagnostic virology studies and on the cytotoxicity of chemicals, pharmaceuticals, and materials. Cultures of these cells are also important for diagnostic genetics, such as when the genetic material of the cells is examined for chromosomal abnormalities during karyotyping. In another application of diagnostic genetics, amniocentesis, fetal cells are extracted from amniotic fluid, cultured, and processed for chromosome analysis.

These studies variously involve cell growth, incubation, immunodiagnostic testing, or other processing often including transfer of cells to a microscope slide. Many of these procedures require or benefit from centrifugation. See, e.g., Gleaves, C. A.; Wilson, D. J.; Wold, A. D.; and Smith, T. F., "Detection and Serotyping of Herpes Simplex Virus in MRC-5 Cells by Use of Centrifugation and Monoclonal Antibodies 16 Hours Postinoculation", 21 *J. Clin. Microbiol.* 29–32 (1985).

Presently, mammalian cells are grown in a variety of culture tubes, flasks, and petri dishes. Anchorage-dependent cells which must attach to a non-toxic substrate during growth are typically grown in culture tubes. Each conventional culture tube, however, exhibits one or more limitations during determination of cell viability and the subsequent testing, treating and processing required in cytological studies, particularly infectious disease diagnostic studies. In one such apparatus, a 16×125 mm glass tube with screw cap closure, cells are grown directly on the curved surface of the tube when it is placed horizontally. The curved surface renders microscopic examination quite difficult since only a fraction of the microscopic field is in focus at any one time. Further, the side of the tube presents a large culture surface which requires both large quantities of reagent and a great deal of time to examine. The shape of the tube renders it incompatible with a fluorescent microscope; the cells must therefore be scraped and transferred to a microscope slide. This procedure is time consuming and destroys the integrity of a monolayer culture, which particularly hinders cost-effective and reliable confirmation analysis for viral antigens.

Another culture system, the Ambitube, available from Flow Laboratories, is similar to the glass tube except that one of its sides is flattened to serve as the bottom and the tube is made of plastic. The Ambitube shares many of the disadvantages of the glass tube, including a large culture surface requiring time-consuming examination and large volume of reagents and a shape that is unsuited for a fluorescent microscope.

The Leighton tube, available from Costar, is also a horizontal culture system with a flattened side. It is plastic and contains a 9×55 mm paddle-like plastic insert on which cells are grown. The insert is often warped and rarely lies uniformly along the flattened side, making it difficult to examine the cells: the varying distance alters the focal plane and therefore requires constant refocussing of a microscope when scanning through the side of the tube to determine cell viability and cytopathology. The insert again provides an undesirably large surface area and, since plastic is itself fluorescent, is incompatible with a fluorescent microscope.

Yet another disadvantage is that cells grown in these three tubes cannot be directly centrifuged but must be transferred from the substrate on which they have grown. Another tube, the Shell vial, overcomes this problem because it is a vertical culture system having a flat bottom opposite the opening in the tube. The Shell vial contains a loose, unsecured 12 mm diameter glass coverslip which serves as the substrate for growing cells. As presently manufactured, however, the bottom of the glass vial is slightly thicker around its periphery, which creates an optical distortion making it diffcult to view cells through the bottom. Further, the plastic plug cap presently used to seal the Shell vial is thickened and of low optical translucence. Both of these features hinder determination of cell viability and cytopathology while the vial is sealed. More importantly, attempts to remove the coverslip can be exasperating and time consuming. Once removed, the loose cover slip is difficult to manipulate.

Another difficulty shared by the above culture tubes involves the culture medium which must surround the cells to ensure their viability. Unless the tubes are completely filled with culture medium, attached cells will dry out and die unless the proper orientation of the tube is maintained. This presents a severe problem during shipment, typically resulting in a 30% mortality rate of transported cell cultures.

In another art, there is a removable measurement partition which, when inserted in a specimen tube, quantifies the volume of a liquid sample. The "Click Stick," available from V-Tech, Inc., has a notch in the partition which accommodates a pipette for withdrawing liquid, such as a urine sample, held beneath the partition.

SUMMARY OF INVENTION

It is therefore an object of this invention to provide an improved culture system for growing, treating and processing cells.

It is a further object of this invention to provide such a culture system which can operate in an upright, vertical position.

It is a further object of this invention to provide such a culture system which can be centrifuged.

It is a further object of this invention to provide such a culture system which has both high and uniform optical clarity, allowing favorable viewing of cells to determine cell viability and cytopathology while the culture system remains sealed.

It is a further object of this invention to provide such a culture system which lends itself to space-efficient storage.

It is a further object of this invention to provide such a culture system having a readily-removable culture unit which carries a culture substrate.

It is a further object of this invention to provide such a culture system with removable culture unit which prevents damage to cultured cells by eliminating the need to transfer cells to a separate substrate.

It is a further object of this invention to provide such a culture system with removable culture unit which can carry a substrate suitable for any anchorage-dependent cell.

It is a further object of this invention to provide such a culture system with removable culture unit which can carry a substrate suitable for fluorescent immunoassay and enzyme immunoassay tests.

It is a further object of this invention to provide such a culture system with removable culture unit which conserves reagent during testing and processing.

It is a further object of this invention to provide such a culture system with removable culture unit which permits fixing and staining cells directly inside the culture system.

It is a further object of this invention to provide such a culture system with removable culture unit wherein the substrate can be easily removed for mounting on a microscope slide.

It is a further object of this invention to provide such a culture system with removable culture unit which affords easy manipulation of the substrate for treating cells when the culture unit is removed.

It is a further object of this invention to provide an improved culture system which maintains culture medium around cells regardless of the orientation of the culture system.

It is a further object of this invention to provide such a culture system which conserves culture medium.

This invention results from the realization that a truly effective culture system accommodating growth, testing and processing of cells on a culture substrate within a tube and, when required, permitting facile removal of the substrate from the tube can be achieved using a culture tube having a bottom opposite its opening, a platform for carrying the substrate proximate the bottom, a handle for positioning and manipulating the platform, and closure means to seal the tube.

This invention features a vertical culture system with removable culture unit. There is a culture tube having an opening and a bottom opposite the opening, and a removable culture unit including a platform and an elongate handle for disposing the platform proximate the tube bottom and for permitting removal of the culture unit. There is also a culture substrate carried by the platform and closure means for sealing the tube.

In one embodiment, the platform is shaped to fit against the inner surface of the tube bottom; the inner surface of the tube bottom may be flat. When the substrate is removable from the platform, the removable culture unit may include means, such as a projection disposed on the handle, for securing the substrate to the platform. The substrate may extend beyond the platform in at least one area. The platform includes a ridge disposed along a portion of the perimeter of the platform and rising above the platorm; when the substrate is removable the ridge may be shaped to accommodate the substrate. The platform is mounted transversely to the handle, the handle extends longitudinally along the tube and the closure means may include means, such as a bearing surface in the closure means, forconstraining the handle to secure in position the removable culture unit.

The culture system may further include a volume retention element having a cross section shaped to fit sealingly against the inner periphery of the tube and having a recess for sealingly engaging the handle. The volume retention element includes a member accessible through the opening of the culture tube to permit withdrawal of the volume retention element. Preferably, a portion of the handle of the removable culture unit is tapered at the region of engagement with the volume retention element and the member is a haft extending transversely from the cross section of the volume retention element. The closure means engages the member to secure the volume retention element inside the tube, which may in turn secure in position the removable culture unit.

In a preferred embodiment, the tube bottom, the platform, and the substrate are optically transparent. The tube bottom may be uniformly transparent and the closure means and volume retention element may be optically translucent. The tube bottom has a thickness of 0.040 to 0.050 inch, the platform has a thickness of 0.0215 to 0.0250 inch, and the substrate has a thickness of 0.0051 to 0.0067 inch. The tube bottom and the platform may be composed of polystyrene and the substrate is glass. The tube is cylindrical and the closure means is a cap which develops a friction seal with the tube. The culture substrate may be the platform itself.

DISCLOSURE OF PREFERRED EMBODIMENT

Other objects, features and advantages will occur from the following description of a preferred embodiment and the accompanying drawings, in which.

This invention may be accomplished by a vertical culture system with removable culture unit in which there is a culture tube having a bottom opposite its opening, a platform disposed proximate the bottom of the tube and carrying a culture substrate, and an elongate handle associated with the platform to place the platform proximate the bottom and permit removal of the platform, and closure means to seal the tube. A vertical culture system with removable culture unit according to this invention provides a culture substrate on which not only growth, but most testing and processing of attached cells can be performed without removing the cells from the substrate and often without removing the substrate from the tube. Such a vertical culture system may further include a volume retention element which maintains culture medium about the cells on the substrate when the culture system is stored in other than an upright position.

Preferably, the culture substrate is removable and is securely carried in a fixed position by the removable culture unit. The platform may include guide ridges to aid positioning of the substrate and to reduce the volume of reagent required for testing. The tube bottom, the platform, and the substrate may be optically transparent to allow microscopic examination of the cells attached to the substrate while the vertical culture system is sealed. The closure means, and the volume retention element when included, may be optically translucent to permit illumination of cells on the substrate so they are viewable through the tube bottom.

Figure 1:
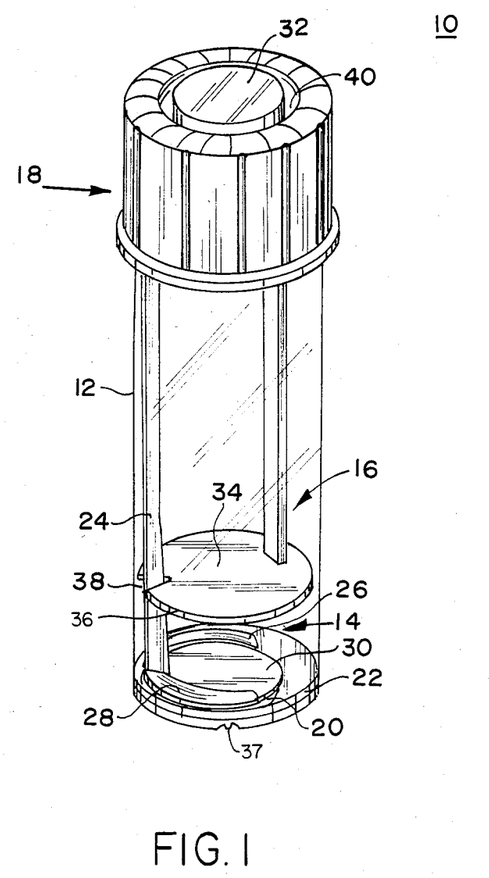
FIG. 1 is an axonometric view of a vertical culture system according to this invention.

Vertical culture system 10, FIG. 1, is an optically transmissive embodiment of the present invention and includes culture tube 12, removable culture unit 14, volume retention element 16, and cap 18. Removable culture unit 14 includes platform 20, disposed proximate tube bottom 22, and handle 24. Platform 20 includes guide ridges 26, 28 and carries removable culture substrate 30.

Cells attached to substrate 30 are easily viewed through tube bottom 22 using an inverted stage microscope. Illumination passes through optically translucent window 32 of cap 18 and, when volume retention element 16 is present, through translucent volume-reducing portion 34. Culture tube 12 is formed by injection-molding of a plastic material. Gatemark 37, formed during injection-molding, is located at the edge of tube 12 rather than under bottom 22 so that bottom 22 retains a uniform transparency throughout. A cell monolayer can therefore be cultured over a small area which is easily examined to determine cell viability and cytopathology or to study fixed and stained cell cultures while substrate 30 remains in culture tube 12.

Substrate 30 is a material such as glass which will support growth of desired attachment-dependent cells. Handle 24 provides a convenient way to manipulate substrate 30 once removable culture unit 14 is extracted from tube 12 to expose attached cells to fixative, stains, or immunodetection reagents. Substrate 30 can be readily dipped into separate solutions and removed from platform 20 for mounting on a microscope slide. When substrate 30 is glass, it is compatible with both fluorescent immunoassay and enzyme immunoassay tests. Guide ridges 26, 28 accommodate and control the position of substrate 30 and greatly reduce the volume of expensive reagent required to stain cells on substrate 30 when carried by platform 20.

The vertical orientation of culture tube 12 renders culture system 10 more space-efficient than horizontal culture tubes and enables centrifugation of substances onto substrate 30. When culture system 10 is used in viral diagnostics, the test sample can be centrifuged onto a culture attached to substrate 30 to improve viral isolation results.

To protect culture cells from drying during storage or shipment, volume retention element 16 is placed inside culture tube 12 so that rim 36 sealingly engages the inner periphery of tube 12. Notch or recess 38 in rim 36 accommodates handle 24 and sealingly engages against it. Handle 24 is thereby positioned proximate or against the inner surface of tube 12. Surface tension and the viscosity of a culture medium or other fluid placed beneath volume-reducing portion 34 aid retention of the fluid around substrate 30. Not only is culture medium thereby maintained around cultured cells but medium costs are greatly reduced as well.

Volume retention element 16 is secured in position by an inner protrusion of cap 18 which defines trough 40. This arrangement is shown more clearly in FIG. 2 for culture system 10. Circular trough 40 is formed by the depression of a portion of cap 18 to form inverted bearing surface 42. A bead along the side of inverted bearing surface 42 forms annular friction ring 44 which frictionally seals cap 18 with culture tube 12. Cap 18 is made of polypropylene and window 32 has a thickness of approximately 0.05 inch. One portion of bearing surface 42 contacts handle 24 to position platform 20 directly against tube bottom 22. Handle 24 is also secured in position by volume controller 16 which is in turn held by detent 46 disposed on a portion of bearing surface 42.

Figure 2:
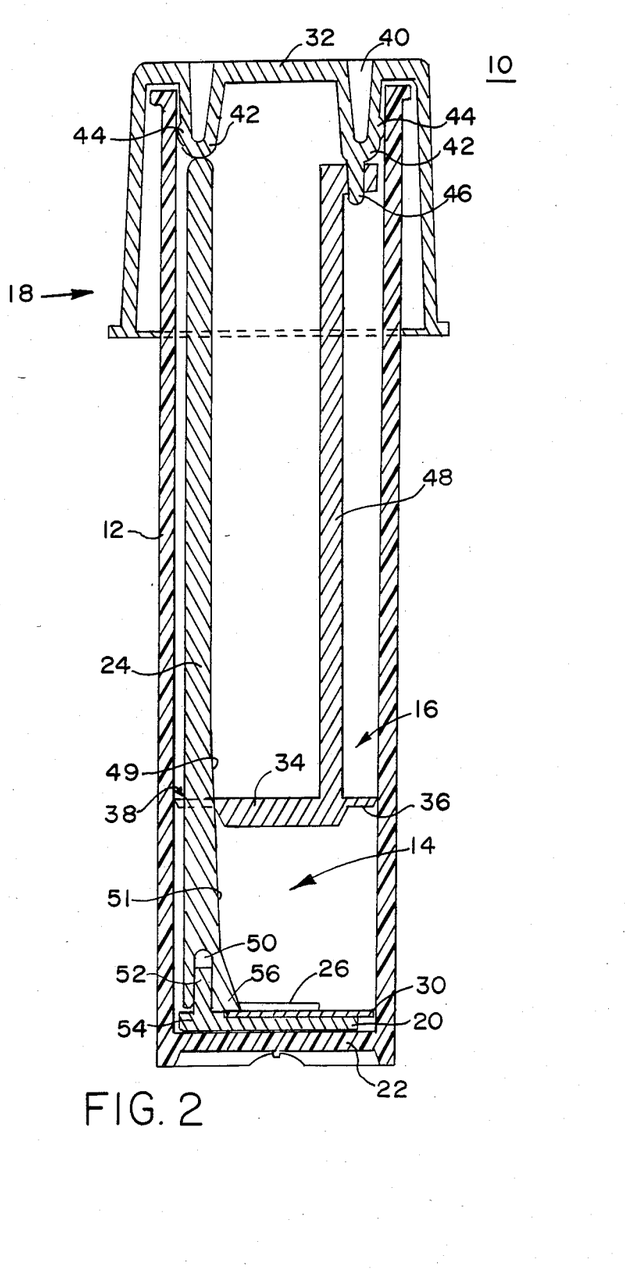
FIG. 2 is an elevational cross-sectional view of the culture system of FIG. 1.

Volume retention element 16 includes shaft 48 which engages detent 46 at one end and volume-reducing portion 34 at the other end. Volume retention element 16 is also made of polypropylene formed such that volume-reducing portion 34 has a central thickness of approximately 0.04 inch and a thickness of 0.01 inch along rim 36. Handle 24 is tapered between points 49 and 51 to ensure a wedging seal with recess 38 of volume retention element 16.

Culture tube 12, handle 24, and platform 20 are made of polystyrene. This material is particularly suited for platform 20 and tube bottom 22 since it provides high optical clarity for viewing cells on substrate 30. Culture tube 12 has a length of approximately 2.6 inch and a diameter of 0.67 inch. Bottom 22 has a thickness ranging from 0.040 to 0.050 inch, platform 20, shaped to fit against flat tube bottom 22, has a thickness ranging from 0.0215 to 0.0250 inch, and substrate 30 is a 12 mm diameter glass coverslip having a thickness from 0.0051 to 0.0067 inch. These thicknesses are selected to provide optimal focusing for viewing cells on substrate 30 through bottom 22 with an inverted stage microscope.

Figures 3A, 3B:
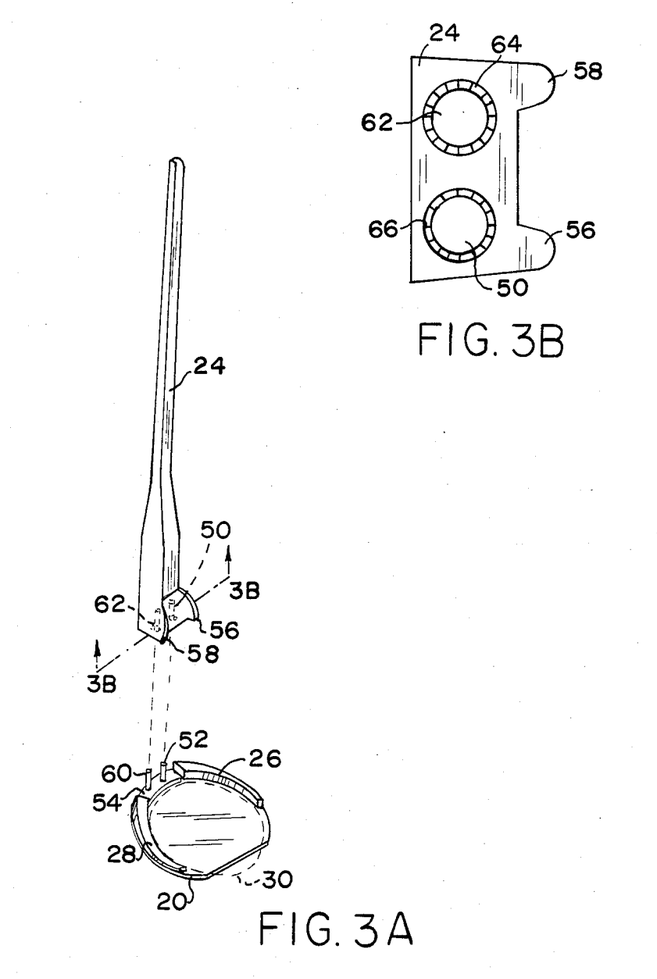
FIG. 3A is an exploded axonometric view of the removable culture unit of FIGS. 1 and 2.
FIG. 3B is a bottom plan view along the lines 3B—3B of FIG. 3A.

Handle 24 contains bores 50, 62 (see FIG. 3A), to receive pins 52, 60 (see FIG. 3A). A portion of the bottom of handle 24 sits upon pin pedestal 54. The attachment between handle 24 and platform 20 afforded by the close fit of pin 52 into bore 50 can be augmented by heat-bonding. Another portion of handle 24 is extended to form projections 56 and 58 (see FIG. 3A) for securing substrate 30 to removable culture unit 14. Pin pedestal 54 has a height similar to the thickness of substrate 30 to insure proper positioning of projections 56 and 58 (see FIG. 3A).

Guide ridge 26 in conjunction with ridge 28, FIG. 3A, perform several functions as indicated in FIG. 3A. Ridges 26, 28 rise approximately 0.02 inch above platform 20 to guide substrate 30, shown in phantom, into proper position on platform 20 so that projections 56, 58 of handle 24 overlap substrate 30 when handle 24 is mounted on pins 52, 60 and pin pedestal 54. Substrate 30 is shown extending beyond an area of platform 20 to allow manipulation of substrate 30 required to insert and remove it from culture unit 14. Alternatively or in addition to projections 56, 58, substrate 30 may be secured by grooves in ridges 26, 28 such that a portion of each ridge overlaps substrate 30.

Alternatively, platform 20 can serve as the substrate onto which cells can be attached and grown. Whether platform 20 or coverslip 30 serves as a culture substrate, another function performed by guide ridges 26, 28 is conservation of expensive reagents. Aided by the surface tension of a reagent, only 25 $\mu$l to 50 $\mu$l of immunodiagnostic reagent, such as antibody in diluent, is required to conduct immunoassay procedures, for example.

Vertical culture system 10 is also effective for culturing any cell that can be grown in suspension. These suspended cells can then be used for isolating infectious agents that grow in suspensions of cultured cells. For example, AIDS virus obtained from serum can be isolated by replication in cells grown in suspension in vertical culture system 10. After incubation, the infected host cells can be centrifuged onto substrate 30. After centrifugation, the culture medium is removed by aspiration and the infected host cells are stained with immunodiagnostic reagents which reveal the presence of the virus.

The openings of pin bores 50, 62 and the bottom surface of projections 56, 58 are shown in FIG. 3B. Handle 24 contains chamferred edges 64 and 66 for pin bores 62, 50, respectively.

Figures 4, 5:
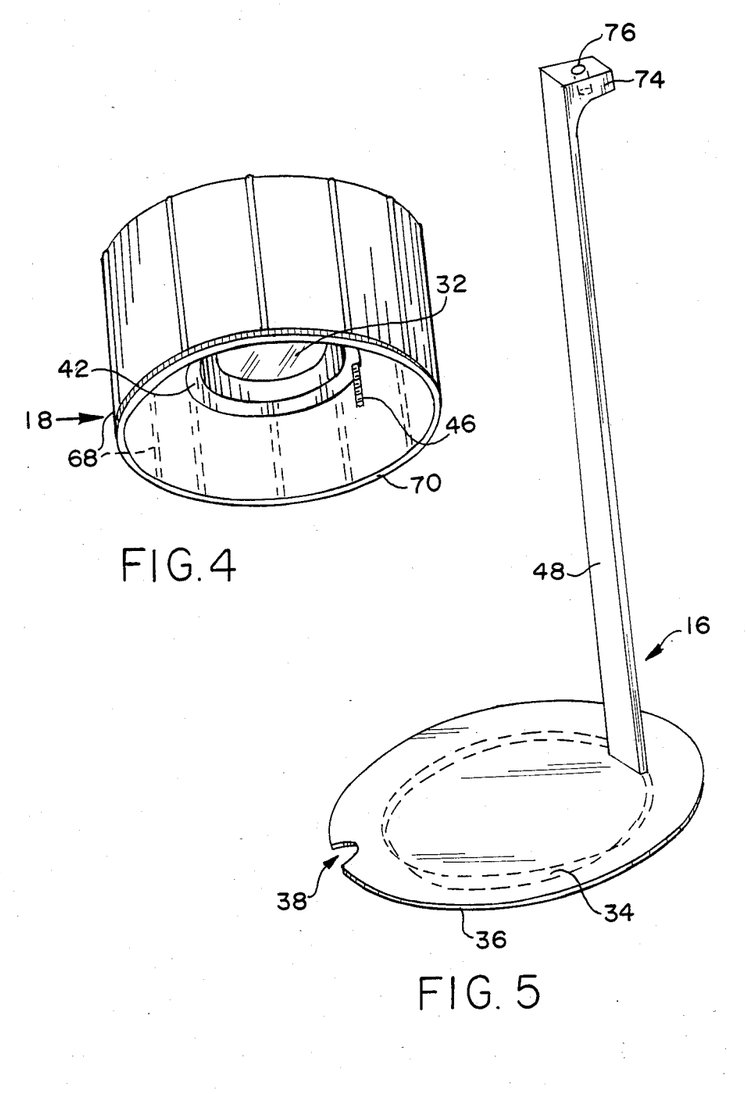
FIG. 4 is an axonometric view into the cap of FIGS. 1 and 2 showing the inverted bearing surface and detent.
FIG. 5 is an axonometric view of the volume retention element of FIGS. 1 and 2.

An axonometric bottom view of cap 18, FIG. 4, shows bearing surface 42 and the underside of translucent window 32. Cap 18 includes ribs 68 and thickened rim 70 to provide increased structural strength.

Detent 46 is flattened on one side to securely engage volume controller 16, FIG. 5. Notch 38 in rim 36 is shaped to sealingly engage handle 24 (not shown). Dashed lines indicate the thickened area of volume-reducing portion 34. Haft 48 is attached to portion 34 and ends in block 74 containing bore 76 for receiving detent 46, FIG. 4.

Figure 6:
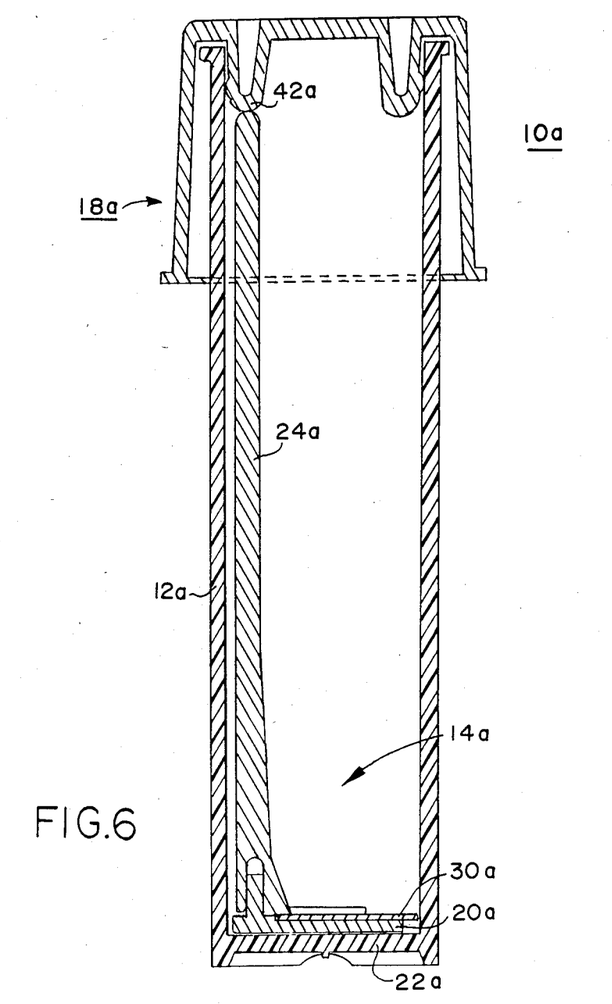
FIG. 6 is an elevational cross-sectional view of another culture system according to this invention without the volume retention element.

Although the previous figures have shown a vertical culture system including a volume retention element, this is not a limitation of the invention as indicated by vertical culture system 10a, FIG. 6. Platform 20a of removable culture unit 14a is held firmly against tube bottom 22a by contact of bearing surface 42a with handle 24a. In this embodiment, it is not necessary for cap 18a to have a detent for engaging a volume retention element. Removable culture unit 14a securely carries substrate 30a during cell growth and processing such as centrifuging. When removal is required, removable culture unit 14a is a convenient device for manipulating substrate 30a.

Although specific features of the invention are shown in some drawings and not others this is for convenience only as each feature may be combined with any or all of the other features in accordance with the invention.

Other embodiments will occur to those skilled in the art and are within the following claims:

What is claimed is:

1. A vertical culture system comprising:
   a culture tube having an opening and a bottom opposite said opening;
   a removable culture unit including a platform and an elongate handle for disposing said platform proximate said tube bottom and for permitting removal of said culture unit;
   an independent culture substrate removably carried by said platform;
   closure means for sealing said tube;
   said platform being mounted transversely to said handle and said handle extending longitudinally along said tube; and
   a volume retention element having a cross section shaped to fit sealingly against the inner periphery of said tube and having a recess for sealingly engaging said handle, said volume retention element including a member accessible through said opening of said culture tube to permit withdrawal of said volume retention element.

2. The culture system of claim 1 in which said platform is shaped to fit against the inner surface of said tube bottom.

3. The culture system of claim 2 in which said inner surface of said tube bottom is flat.

4. The culture system of claim 1 in which said removable culture unit includes means for securing said substrate to said platform.

5. The culture system of claim 1 in which said substrate extends beyond said platform in at least one area.

6. The culture system of claim 1 in which said closure means includes means for constraining said handle to secure in position said removable culture unit.

7. The culture system of claim 6 in which said means for constraining is a bearing surface in said closure means.

8. The culture system of claim 1 in which a portion of said handle of said removable culture unit is tapered at the region of engagement with said volume retention element.

9. The culture system of claim 1 in which said member is a haft extending transversely from said cross section of said volume retention element.

10. The culture system of claim 1 in which said closure means engages said member to secure said volume retention element inside said tube.

11. The culture system of claim 10 in which said removable culture unit is secured in position by said volume retention element.

12. The culture system of claim 11 in which said volume retention element is optically translucent.

13. The culture system of claim 1 in which said tube bottom is optically transparent.

14. The culture system of claim 13 in which said tube bottom is uniformly transparent.

15. The culture system of claim 1 in which said platform is optically transparent.

16. The culture system of claim 1 in which said substrate is optically transparent.

17. The culture system of claim 1 in which said closure means is optically translucent.

18. The culture system of claim 1 in which said tube bottom has a thickness of 0.040 to 0.050 inch, said platform has a thickness of 0.0215 to 0.0250 inch, and said substrate has a thickness of 0.0051 to 0.0067 inch.

19. The culture system of claim 18 in which said tube bottom and said platform are composed of polystyrene and said substrate is glass.

20. The culture system of claim 1 in which said tube is cylindrical.

21. The culture system of claim 1 in which said closure means is a cap which develops a friction seal with said tube.

22. A vertical culture system comprising:
   a culture tube having an opening and a bottom opposite said opening;
   a removable culture unit including a platform and an elongate handle for disposing said platform proximate said tube bottom and for permitting removal of said culture unit;
   an independent culture substrate removably carried by said platform;
   closure means for sealing said tube; and
   said removable culture unit includes means for securing said substrate to said platform, said means for securing including at least one projection disposed on said handle.

23. A vertical culture system comprising:
   a culture tube having an opening and a bottom opposite said opening;
   a removable culture unit including a platform and an elongate handle for disposing said platform proximate said tube bottom and for permitting removal of said culture unit;
   an independent culture substrate removably carried by said platform;
   closure means for sealing said tube; and said platform including a ridge disposed along a portion of the perimeter of said platform and rising above said platform.

24. The culture system of claim 23 in which said substrate is removable and said ridge is shaped to accommodate said substrate.

25. A vertical culture system comprising:
 a culture tube having an opening and a bottom opposite said opening;
 a removable culture unit including a platform and an elongate handle for disposing said platform proximate said tube bottom and for permitting removal of said culture unit;
 a culture substrate carried by said platform;
 a volume retention element having a cross section shaped to fit sealingly against the inner periphery of said tube and having a recess for sealingly engaging said handle, said volume retention element including a member accessible through said opening of said culture tube to permit withdrawal of said volume retention element; and
 closure means for sealing said tube.

* * * * *